United States Patent [19]

Slocum

[11] Patent Number: 4,528,987

[45] Date of Patent: Jul. 16, 1985

[54] APPARATUS AND PROCESS FOR COMMUNICATING AN ELECTROGRAM

[75] Inventor: Chester D. Slocum, Miami, Fla.

[73] Assignee: Cordis Corporation, Miami, Fla.

[21] Appl. No.: 536,617

[22] Filed: Sep. 28, 1983

[51] Int. Cl.³ ............................................. A61B 5/04
[52] U.S. Cl. .................................. 128/696; 128/903; 128/419 PT
[58] Field of Search ....... 128/419 P, 419 PS, 419 PT, 128/419 PG, 631, 903, 908; 340/870.1, 870.31

[56] References Cited

U.S. PATENT DOCUMENTS

| | | | |
|---|---|---|---|
| 3,253,588 | 5/1966 | Vuilleumier et al. | 128/903 |
| 3,713,124 | 1/1973 | Durland et al. | 340/870.31 |
| 3,794,841 | 2/1974 | Cosentino et al. | 128/908 |
| 3,893,111 | 7/1975 | Cotter | 128/631 |
| 3,942,535 | 3/1976 | Schulman | 128/419 PS |
| 3,986,495 | 10/1976 | Miller | 128/908 |
| 4,223,679 | 9/1980 | Schulman et al. | 128/419 PT |
| 4,231,027 | 10/1980 | Mann et al. | 128/419 PT |
| 4,281,664 | 8/1981 | Duggan | 128/419 PT |
| 4,324,251 | 4/1982 | Mann | 128/419 PT |
| 4,361,153 | 11/1982 | Slocum et al. | 128/419 P |
| 4,416,283 | 11/1983 | Slocum | 128/419 PG |
| 4,450,431 | 5/1984 | Hochstein | 340/870.31 |

Primary Examiner—William E. Kamm
Assistant Examiner—Mitchell J. Shein
Attorney, Agent, or Firm—George H. Gerstman

[57] ABSTRACT

An apparatus and a process are disclosed for communicating an electrogram from a patient. An enclosure having a tuned coil mounted therein is implanted in the patient. The tuned coil is adapted to reradiate a signal in the presence of an externally generated carrier signal. A variable impedance device is provided across the tuned coil. The resistance of the variable impedance device can be altered linearly and it is set at a reference level that is approximately the center of its linear range. An analog signal, representative of the electrogram, is coupled to the input of the variable impedance device. In this manner, the variable impedance device will be modulated in response to the electrogram.

16 Claims, 3 Drawing Figures

APPARATUS AND PROCESS FOR COMMUNICATING AN ELECTROGRAM

BACKGROUND OF THE INVENTION

The present invention concerns a novel apparatus and process for communicating an electrogram from a patient. This application is related to U.S. patent application Ser. No. 514,514, filed July 18, 1983 and entitled "Analog Telemetry System For Biomedical Implant."

In U.S. Pat. No. 4,361,153, issued Nov. 30, 1982 and assigned to the assignee of the present invention, there is disclosed the use of a resonant impedance modulated transponder, in a device implanted in the patient, to modulate the phase of a relected magnetic signal that is the product of a magnetic carrier imposed from outside of the body. In this manner, information is transmitted from a fixed internal implant to a positionable external telemetry unit. A relatively high energy magnetic field at a carrier frequency is established by a transmitter in the external unit. The field permates the skin, underlying tissue and case of the implant and induces a signal in a resonant, impedance modulated transponder in the implant tuned to the carrier frequency. A second field is reradiated or reflected at the carrier frequency by the resonant transponder. The transponder's impedance is varied in accordance with a modulation input signal, causing a shift in the phase angle and amplitude of the transponder's contribution to the composite reflected signal, thereby resulting in a proportional phase and amplitube shift in the composite reflected signal. The composite reflected signal is picked up and demodulated by a phase shift detector in the external telemetry unit.

In the primary embodiment disclosed in U.S. Pat. No. 4,361,153, the modulation input signal is a pulse width modulated binary signal that is generated by the implant. The patent also discloses that the modulation input signal may be an analog input signal.

It has been found that a resonant impedance modulated transponder in an implant can be utilized in connection with communicating an electrogram from a patient. It has been discovered that such communication can be effective utilizing an analog representation of the electrogram, such as the analog amplified electrogram signal itself. In this manner, the necessity for digitizing an analog signal and providing a pulse width modulated binary signal is obviated. Systems in which the analog signal must be digitized require an analog to digital converter and also a subsequent digital to analog converter, but in accordance with the present invention a system is provided in which such converters are unnecessary to achieve the desired result.

It is an object of the present invention to provide an apparatus and process for communicating an electrogram from a patient, in a manner that is accurate and efficient and results in an electrogram signal outside of the body that corresponds as close as possible to the patient's electrogram.

Another object of the present invention is to provide apparatus for communicating an electrogram from a patient, which uses a minimum amount of parts in the implant yet produces a high quality EKG.

A further object of the present invention is to provide an apparatus and process for communicating more than one waveform at a time from a patient.

A still further object of the present invention is to provide an apparatus and process for communicating an electrogram from a patient, which is simple in construction and easy to manufacture.

Other objects and advantages will become apparent as the description proceeds.

SUMMARY OF THE INVENTION

In accordance with the present invention, apparatus is provided for communicating an electrogram from a patient. The apparatus comprises an implantable enclosure with a tuned coil mounted within the enclosure. Variable impedance means are connected across the tuned coil and means are provided for coupling an analog representation of the electrogram to an input of the variable impedance means. In this manner, the impedance of the variable impedance means will be modulated in response to the electrogram.

The variable impedance means comprises a device whose resistance can be altered linearly. The device is set at a reference level that is approximately the center of its linear range.

In one embodiment of the invention, the device comprises a pair of FETs biased in the approximate center of their linear range.

In another embodiment of the invention, the device comprises a pair of matched transistors, each having a diode across its emitter-collector circuit, with the input comprising the bases of the transistors.

In a third embodiment, the device comprises an optical coupler, and means are provided for setting the optical coupler at a reference level that is approximately the center of its linear range.

Also in accordance with the present invention, a process is provided for communicating an electrogram from a patient. The process comprises the steps of implanting in the patient an enclosure having a tuned coil mounted therein. The tuned coil is adapted to reradiate a signal in the presence of an externally generated carrier signal. A variable impedance device is provided across the tuned coil, with the variable impedance device having a resistance that can be altered linearly. The variable impedance device is set at a reference level that is approximately the center of its linear range. The input of the variable impedance device is coupled to an analog representation of the electrogram. In this manner, the variable impedance device will be modulated in response to the electrogram.

A more detailed explanation of the invention is provided in the following description and claims, and is illustrated in the accompanying drawings.

DETAILED DESCRIPTION OF THE ILLUSTRATIVE EMBODIMENT

Figure 1:
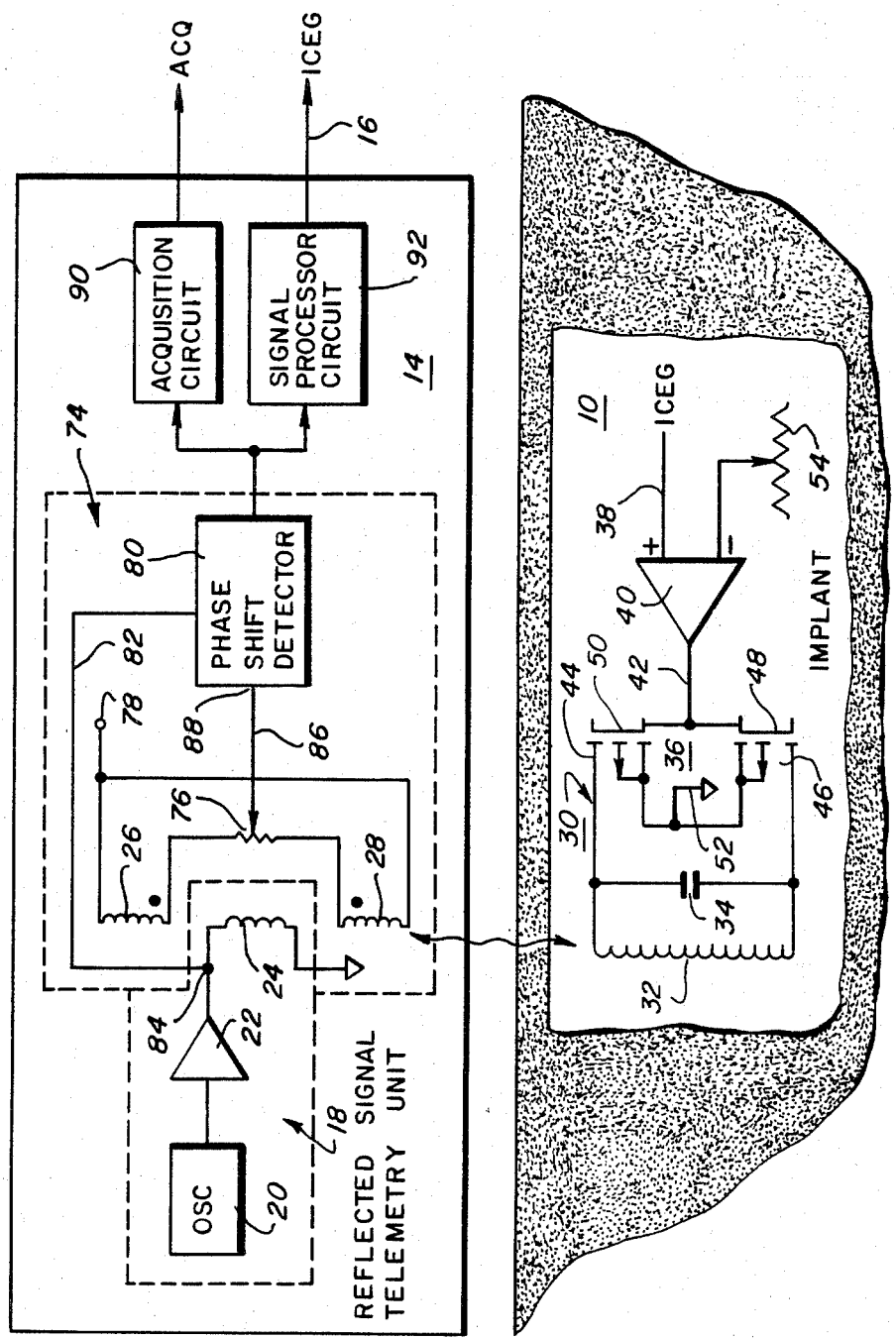
FIG. 1 is a block diagram of an apparatus for communicating an electrogram, constructed in accordance with the principles of the present invention.

Referring to FIG. 1, an enclosure 10 is implanted within the patient's body 12. An external reflected signal telemetry unit 14 is illustrated for receiving the reflected signal and providing an output representing the electrogram via line 16. In the illustrative embodiment, the electrogram is an intracardiac electrogram (ICEG). However, it is understood that the present invention is applicable to other electrograms, including intraneural and intramuscular electrograms.

The external reflected signal telemetry unit 14 includes a carrier transmitter 18 having an oscillator 20 which produces a continuous wave myriametric frequency electrical output at a selected frequency. The oscillator output is fed via a driver amplifier 22 to the middle coil 24 in a triple coil assembly comprising coils 24, 26 and 28.

In the implant 10, a reflected signal transponder 30 includes a coil 32 the ends of which are connected in parallel with a capacitor 34 and a variable impedance means 36 which forms the load into which the tuned coil (coil 32 and capacitor 34) is terminated electrically. The resonant or band pass frequency of the tuned coil is centered at the carrier frequency.

The oscillating current through the coil 24 in the telemetry unit establishes a magnetic field which radiates into the adjacent implant and induces a corresponding voltage in tuned coil 32 which in turn reradiates a secondary magnetic field at the same carrier frequency. However, when conducting, variable impedance means 36 acts as a low resistance shunt across the tuned coil which removes the capacitive reactance of the transponder and alters the phase of the reflected signal.

The input to variable impedance means 36 is the amplified intracardiac electrogram which is provided by feeding the actual intracardiac electrogram via line 38 to amplifier 40 from which it is fed via line 42 to variable impedance means 36.

In the FIG. 1 embodiment, variable impedance means 36 comprises a matched pair of FETs 44 and 46 with input line 42 connected directly to common gates 48 and 50, with the drains of the FETs connected to the tuned coil and the sources connected to ground 52. In the illustrative embodiment, FETs 44 and 46 comprise P-type MOS FETs.

A significant feature of the present invention is that the FETs are set at a reference level that is approximately the center of their linear range. Thus each FET is linear from where pinch-off ends (i.e., where conduction begins) to saturation. A bias potentiometer 54 is provided and the arm is adjusted so that when there is no signal on line 38, FETs 44 and 50 will be biased to approximately the center of their linear range. As an example, although no limitation is intended, if FETs 44 and 46 have a characteristic curve in which pinch-off ends at one volt and saturation is complete at four volts, they would be biased at approximately 2.5 volts. In this manner, the resistance of the FETs will vary both ways in accordance with both negative and positive going analog signals on line 42.

One manner of adjusting potentiometer 54 is to provide a voltage at gates 48 and 50 which is somewhere within the linear range of the FETs 44 and 46 and then to adjust potentiometer 54 so that the clipping is equal on both sides.

Figure 2:
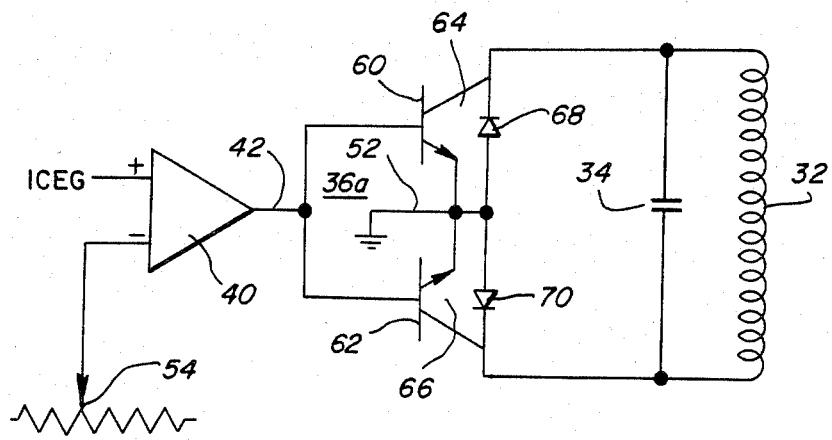
FIG. 2 is a schematic circuit diagram of a modified form of the implant device of the apparatus of FIG. 1.

In a modified form of the invention, another variable impedance means 36a is illustrated in FIG. 2. The same reference numerals are used in FIG. 2 for items which are identical to the items of FIG. 1. However, in the FIG. 2 embodiment, line 42 is connected to common bases 60 and 62 of NPN transistors 64 and 66, respectively. A diode 68 is connected across the emitter collector circuit of transistor 64 and a diode 70 is connected across the emitter collector circuit of transistor 66. The cathode of diode 68 is connected to the collector while the anode is connected to ground. Likewise, the cathode of diode 70 is connected to the collector while the anode is connected to ground.

The circuit of FIG. 2 operates similarly to the implant circuit of FIG. 1. Potentiometer 54 is varied so that the matched transistors 64 and 66 are biased to the center of their linear range.

Figure 3:
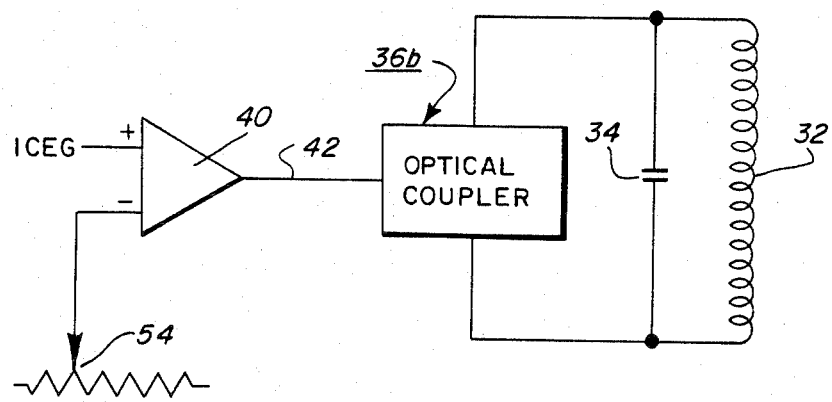
FIG. 3 is a schematic circuit diagram of another modified form of the implant device of the apparatus of FIG. 1.

FIG. 3 shows another modified form of the invention, in which an optical coupler 36b is utilized as the variable impedance means. Potentiometer 54 is adjusted so that optical coupler 36b is set at a reference level that is approximately the center of its linear range.

Referring back to FIG. 1, in a receiver 74 of telemetry unit 14, corresponding ends of the outer pickup coils 26 and 28 are interconnected by a potentiometer 76 and the other ends are connected to a positive DC voltage at point 78. A phase shift detector 80 is connected via line 82 to point 84 in the output to the oscillator coil 24 in order to receive the carrier signal as a reference input. The wiper 86 of potentiometer 76 picks off a signal induced in the pickup coils 26 and 28 which signal is inputted at point 88 to phase shift detector 80. By comparing the signal at point 84 with the signal at point 88, the phase shift detector 80 produces an output level indicative of the displacement of the phase angle of the received signal at point 88 relative to the carrier signal at point 84. When telemetry unit 14 is in position for transmission, the signal at point 88 will include the reflected signal from the implanted transponder 10 as well as the attenuated carrier.

The phase angle output level of the detector 80 is passed to an acquisition circuit 90 which produces a signal indicative of acquisition when the output level of detector 80 exceeds a threshold value. During reception of an intracardiac electrogram, the output of phase shift detector 80 is fed to a signal processing circuit 92 which reconstructs the intracardiac electrogram signal being received at point 88.

For additional circuit and parameter details reference is hereby made to U.S. Pat. No. 4,361,153, the disclosure of which is incorporated herein.

It can be seen that a system has been described in which voltage waves from the inside of the heart are reproduced utilizing a myriametric telemetry system that is directly responsive to the analog intracardiac electrogram, and without requiring the digitizing of signals or the use of an A/D converter or a D/A converter which are concomitant with such digitizing.

Although illustrative embodiments of the invention have been shown and described, it is to be understood that various modifications and substitutions may be made by those skilled in the art without departing from the novel spirit and scope of the present invention.

What is claimed is:

1. Apparatus for communicating an electrogram from a patient, which comprises:
    an implantable enclosure;
    a tuned coil mounted within the enclosure;
    variable impedance means connected across the tuned coil;
    means for coupling an analog representation of the electrogram to an input of the variable impedance means whereby the impedance of the variable impedance means will be modulated in response to the electrogram;

the variable impedance means comprising a device having a linearly varying resistance range;

means for setting said device at a reference level that is approximately the center of said range, whereby the resistance of said device reflects positive and negative changes in the electrogram.

2. Apparatus as described in claim 1, said coupling means including means for amplifying the electrogram; said amplifying means including said setting means; and said analog representation comprising the amplified electrogram.

3. Apparatus as described in claim 1, said device comprising a pair of transistors biased in the approximate center of their linear range.

4. Apparatus as described in claim 3, said pair of transistors comprising a pair of FETs and said input comprising the gates of the FETs.

5. Apparatus as described in claim 4, wherein the tuned coil comprises a capacitor and an inductance; the drains of the FETs are connected across the capacitor and inductance and the sources of the FETs are connected to ground.

6. Apparatus as described in claim 3, said pair of transistors comprising a pair of matched transistors each having a diode across its emitter-collector circuit; and said input comprising the bases of the transistors.

7. Apparatus as described in claim 1, said device comprising an optical coupler.

8. Apparatus as described in claim 1, said variable impedance means being operable to alter the phase of a signal reradiated by said tuned coil in the presence of an externally generated carrier signal at the frequency to which said tuned coil is tuned.

9. Apparatus for communicating an electrogram from a patient, which comprises:
an implantable enclosure;
a tuned coil mounted within the enclosure;
variable impedance means connected across the tuned coil;
means for coupling an analog representation of the electrogram to an input of the variable impedance means whereby the impedance of the variable impedance means will be modulated in response to the electrogram;
said coupling means including means for amplifying the electrogram;
said analog representation comprising the amplified electrogram;
the variable impedance means comprising a device having a linearly varying resistance range;
means for setting said device at a reference level that is approximately the center of said range, whereby the resistance of said device reflects positive and negative changes in the electrogram;
said amplyifying means including said setting means;
said variable impedance means being operable to alter the phase of a signal reradiated by said tuned coil in the presence of an externally generated carrier signal at the frequency to which said tuned coil is tuned.

10. Apparatus for communicating an electrogram from a patient, which comprises:
a coil tuned to a selected frequency mounted within said enclosure;
a low impedance shunt circuit connected across said tuned coil including a device for modulating the impedance of said shunt circuit in accordance with an analog signal representative of the electrogram to alter the phase and amplitude of a signal reradiated by said tuned coil in the presence of an externally generated magnetic carrier signal at the frequency to which said coil is tuned;
said device having a linearly varying resistance range; and
means for setting said device at a reference level that is approximately the center of said range, whereby the resistance of said device reflects positive and negative changes in the electrogram.

11. A process for communicating an electrogram from a patient, comprising the steps of:
implanting in the patient an enclosure having a tuned coil mounted therein, said tuned coil being adapted to reradiate a signal in the presence of an externally generated carrier signal;
providing across the tuned coil a variable impedance device having a linearly varying resistance range;
setting said variable impedance device at a reference level that is approximately the center of its linear range;
coupling to the input of the variable impedance device an analog representative of the electrogram, whereby the variable impedance device will be modulated in response to the electrogram.

12. A process as described in claim 11, wherein the externally generated carrier signal is presented at the frequency to which said tuned coil is tuned.

13. A process as described in claim 11, said device comprising a pair of transistors biased in the approximate center of their linear range.

14. A process as described in claim 13, said pair of transistors comprising a pair of FETs and said input comprising the gates of the FETs.

15. A process as described in claim 13, said pair of transistors comprising a pair of matched transistors each having a diode across its emitter-collector circuit, and said input comprising the bases of the transistors.

16. A process as described in claim 11, said device comprising an optical coupler, and said setting step including setting the optical coupler at a reference level that is approximately the center of its linear range.

* * * * *